(12) United States Patent
Vystavel et al.

(10) Patent No.: US 10,105,734 B2
(45) Date of Patent: Oct. 23, 2018

(54) METHOD OF MODIFYING A SAMPLE SURFACE LAYER FROM A MICROSCOPIC SAMPLE

(71) Applicant: FEI Company, Hillsboro, OR (US)

(72) Inventors: Tomas Vystavel, Brno (CZ); Aurelien Philippe Jean Maclou Botman, Hillsboro, OR (US)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/992,743

(22) Filed: Jan. 11, 2016

(65) Prior Publication Data
US 2016/0199878 A1    Jul. 14, 2016

(30) Foreign Application Priority Data

Jan. 12, 2015 (EP) ..................... 15150779

(51) Int. Cl.
  *G01N 35/00* (2006.01)
  *B05D 5/02* (2006.01)
  (Continued)

(52) U.S. Cl.
  CPC .................. *B05D 5/02* (2013.01); *B05C 3/10* (2013.01); *B05D 3/0493* (2013.01); *B05D 5/00* (2013.01);
  (Continued)

(58) Field of Classification Search
  CPC ......... H01L 2924/0002; H01L 2924/00; H01L 21/3212; H01L 2251/5338; H01L 51/5253;
  (Continued)

(56) References Cited

U.S. PATENT DOCUMENTS 5,270,552 A    12/1993 Ohnishi et al.
8,919,902 B2   12/2014 Aoki et al.
(Continued)

FOREIGN PATENT DOCUMENTS

CN    100592466       2/2010
CN    103855083 A     6/2014
(Continued)

OTHER PUBLICATIONS

Steven J. Randolph et al., "Capsule-free Fluid Delivery and Beam-Induced Electrodeposition in a Scanning Electron Microscope", RSC Advances. vol. 3, No. 43, Jan. 1, 2013, 8 pages.
(Continued)

*Primary Examiner* — Tony Tran
(74) *Attorney, Agent, or Firm* — Scheinberg & Associates, P.C.; Michael O. Scheinberg

(57) ABSTRACT

A method of modifying a sample surface layer in the vacuum chamber of a particle-optical apparatus, the method performed in vacuum, the method comprising:
  Providing the microscopic sample attached to a manipulator,
  Providing a first liquid at a first (controlled) temperature,
  Dipping the sample in the first liquid, thereby causing a sample surface modification,
  Removing the sample from the first liquid,
  Providing a second liquid at a second (controlled) temperature,
  Dipping the sample in the second liquid, and
  Removing the sample from the second liquid.
This enables the wet processing of a sample in-situ, thereby enhancing speed and/or avoiding subsequent alteration/contamination of the sample, such as oxidation, etc. The method is particularly useful for etching a lamella after machining
(Continued)

the lamella with a (gallium) FIB to remove the surface layer where gallium implantation occurred, or where the crystal lattice is disturbed.

13 Claims, 2 Drawing Sheets

(51) Int. Cl.
| | |
|---|---|
| *B05C 3/10* | (2006.01) |
| *B05D 3/04* | (2006.01) |
| *B05D 5/00* | (2006.01) |
| *C23C 18/16* | (2006.01) |
| *C25D 5/16* | (2006.01) |
| *C25D 7/12* | (2006.01) |
| *C25D 21/04* | (2006.01) |
| *H01L 21/02* | (2006.01) |
| *H01L 21/306* | (2006.01) |
| *H01L 21/3205* | (2006.01) |
| *H01J 37/20* | (2006.01) |
| *H01J 37/317* | (2006.01) |
| *G01N 1/32* | (2006.01) |
| *G01N 1/44* | (2006.01) |

(52) U.S. Cl.
CPC ............ *C23C 18/1633* (2013.01); *C25D 5/16* (2013.01); *C25D 7/12* (2013.01); *C25D 21/04* (2013.01); *H01J 37/20* (2013.01); *H01J 37/317* (2013.01); *H01L 21/02041* (2013.01); *H01L 21/30604* (2013.01); *H01L 21/32051* (2013.01); *G01N 1/32* (2013.01); *G01N 1/44* (2013.01); *H01J 2237/20* (2013.01); *H01J 2237/2067* (2013.01); *H01J 2237/31745* (2013.01)

(58) Field of Classification Search
CPC .......... G01N 2035/00326; G01N 2035/00495; G01N 35/0092; G01N 35/00; G01N 2015/1006

See application file for complete search history.

(56) References Cited

U.S. PATENT DOCUMENTS

| | | |
|---|---|---|
| 8,919,938 B2 | 12/2014 | Clark et al. |
| 2005/0227484 A1 | 10/2005 | Gu et al. |
| 2006/0105349 A1* | 5/2006 | Ekenberg ............ C12N 15/1017 435/6.12 |
| 2010/0032302 A1 | 2/2010 | Holtermann et al. |
| 2012/0196440 A1 | 8/2012 | Botman et al. |
| 2013/0068611 A1 | 3/2013 | Botman et al. |
| 2013/0205808 A1 | 8/2013 | Mulders et al. |
| 2014/0151335 A1 | 6/2014 | Randolph et al. |
| 2014/0231644 A1 | 8/2014 | Zachreson |
| 2015/0090878 A1 | 4/2015 | Smulders-Weemers et al. |

FOREIGN PATENT DOCUMENTS

| | | |
|---|---|---|
| EP | 2741075 | 6/2014 |
| JP | 2010-133710 | * 12/2008 |
| JP | 2010133710 | 6/2010 |
| JP | 5205234 B2 | 6/2013 |

OTHER PUBLICATIONS

Joachim Mayer et al., "TEM Sample Preparation and FIB-Induced Damage", MRS Bulletin, vol. 32, May 2007, 8 pages.
"Microinjection System", Kleindiek Nanotechnik, Accessed Jan. 11, 2016, 1 page. <http://www.nanotechnik.com/mis-em.html>.
Matthew Bresin et al., "Liquid Phase Electron-Beam-Induced Deposition on Bulk Substrates Using Environmental Scanning Electron Microscopy", Microscopy and Microanalysis, vol. 20, No. 2, Apr. 1, 2014, 9 pages.

* cited by examiner

METHOD OF MODIFYING A SAMPLE SURFACE LAYER FROM A MICROSCOPIC SAMPLE

FIELD OF THE INVENTION

The invention relates to a method of modifying a sample surface layer from a sample in a particle-optical apparatus, the method performed in vacuum.

BACKGROUND OF THE INVENTION

Such a method is known from S J Randolph et al., 'Capsule-free fluid delivery and beam-induced electrodeposition in a scanning electron microscope', RSC Adv., 2013, p 20016-23 [-1-]

Randolph describes the use of a liquid injection system (a nanocapillary) to deposit a droplet of liquid of $CuSO_4$ solution in the low vacuum chamber of an environmental scanning electron microscope (ESEM). Capillary flow of the liquid is induced by bringing a nanocapillary into contact with a substrate. A microscopic droplet is then formed and stabilized (that is: its volume is kept approximately constant) by controlling the droplet evaporation rate with the substrate temperature (cooling the substrate with a Peltier heating/cooling stage) and by controlling the pressure of $H_2O$ vapor injected into the vacuum chamber. A focused electron beam is admitted to the droplet through a pressure limiting aperture so that the electron emitter of the scanning electron microscope can operate at a better vacuum than the vacuum in the low vacuum chamber. Electrochemical reduction of aqueous $Cu^{2+}$ to solid, high purity, deposited Cu is achieved by using the capillary as an anode and the electron beam of the ESEM as a virtual cathode, enabling electrodeposition on both conductive and insulating substrates.

It is noted that the phrase 'particle-optical apparatus' is used to embrace electron microscopes (transmission electron microscopes, scanning electron microscopes, scanning transmission electron microscopes, etc.), focused ion beam machines (FIBs) and combination thereof.

The invention intends to provide an improved and more generic method of modifying the sample surface layer.

SUMMARY OF THE INVENTION

To that end the method of the invention comprises the steps of:
 Providing the microscopic sample attached to a manipulator,
 Providing a first liquid at a first temperature,
 Dipping the sample in the first liquid, thereby causing a sample surface modification,
 Removing the sample from the first liquid,
 Providing a second liquid at a second temperature,
 Dipping the sample in the second liquid, and
 Removing the sample from the second liquid.

Inventors realized that the use of liquids in a vacuum is not only useful for electrodeposition using a virtual cathode, but rather opens a whole new area of wet processing applications of the sample surface when a sample is dipped in a first liquid and then in a second liquid. Such a modification of the sample surface is a modification of the roughness, the hydrophilicity, the surface charge, the surface energy, the biological compatibility or -reactivity, the addition of functional groups, the addition of biological material, the plating of the sample surface or the removal of a sample surface layer.

By dipping the sample in the first liquid, a control of the (wet) processing time is achieved, which is not achieved in the method of Randolph. By dipping the sample in a second liquid the sample can, for example, be rinsed, or a further wet process step may be added.

Preferably the first temperature and the second temperature are controlled temperatures. As the temperature of a liquid in vacuum strongly influences its evaporation rate, and thus the deterioration of the vacuum in which the liquids reside.

It is noted that, although Randolph discloses the use of droplets in vacuum and electro-plating, Randolph is silent of dipping a sample in a liquid. Randolph is also silent of other uses than plating, as Randolph forms the droplet on the sample (the surface) and aims to locally form depositions on those positions where the electron beam is aimed. Contrary to that, applicant's invention is aimed at surface modification of the whole sample surface, or at least the whole sample surface submerged in the liquid.

It is noted that the first and second liquid can be formed on one surface ("substrate"), but may also be formed on two different surfaces ("substrates"). In the latter case the surfaces may differ in e.g. temperature (for controlling the evaporation rate of different liquids) or constitution (showing for example different wetting properties for the different liquids).

Preferably the sample is attached to a manipulator by forming a weld using beam induced deposition, the beam induced deposition induced by a laser beam, an electron beam or an ion beam.

In an embodiment the sample has a dimension of less than 10 μm in any direction and the first liquid and the second liquid are deposited as droplets with a volume of less than 1 pico-liter, more specifically less than 1 femto-liter.

It is noted that when a liquid is exposed to vacuum, evaporation of the liquid occurs. This evaporation deteriorates the vacuum of the apparatus and diminishes the amount of liquid. Control of the evaporation occurs by regulating (controlling) the temperature of the droplet and by the partial pressure of the surrounding vacuum, as well as the flow from the applicator of the liquid (capillary or such). All these factors are needed to stabilize the droplet and droplet volume.

It is noted that, although the use of droplets on a surface of, for example, the stage that is commonly present in a SEM or a FIB, is one form of providing the liquids, other forms of providing may be used as well. Such other forms may include:
 providing small volumes of (temperature controlled) liquids in, for example, recesses of the stage, lowering the temperature of the liquid, and thus the evaporation rate, after use,
 providing small volumes of liquids that are sealed from the vacuum when not in use,
 providing the liquids via small channels in the stage,
 electrospraying of droplets on the surface,
 applying droplets using inkjet techniques (including forming a small steam bubble in a channel or squeezing a droplet out using deformation of the channel using piezo crystals),
 etc.

The method is particularly suitable to modify the surface of a semiconductor sample etching the surface to the required thickness and/or plating the sample with a thin protective layer, such as a layer of platinum.

The method is also well suited to excise a sample from a work piece (for example a wafer or a biological sample) using a focused ion beam, as known from e.g. U.S. Pat. No. 5,270,552 to Hitachi [-2-].

Preferred embodiments of the surface modification are etching, electro-chemical etching, electroless plating or electroplating using a non-virtual cathode.

In these embodiments the first liquid is an etchant or a plating liquid. Etch removal is controllable by controlling the parameters of etchant chemical, submerging time (dipping time), liquid concentration, and liquid temperature (and current in the case of electro-chemical etching).

Likewise plating thickness is controllable by controlling the parameters of plating chemical, submerging time (dipping time), liquid concentration, and liquid temperature (and current in the case of electroplating).

Hereby a fine control of etch removal or plating thickness can be achieved, making the method well suited to remove or add surface layers with a thickness of less than 10 nm, but also for removing or adding much thicker layers.

In the case of electroplating and electro-etching the sample is biased with respect to the liquid, the liquid deriving its potential from e.g. the surface on which it rests.

In a preferred embodiment the second liquid is a rinsing liquid. A rinsing liquid ends the prior step of e.g. etching or plating, and also cleans the surface from any substances present in the first liquid. The rinsing may be repeated several times by dipping the sample several in the rinsing liquid, or repeatedly in different volumes (different droplets, or such like) of the rinsing liquid.

In another embodiment the first liquid contains biological material, thereby applying the biological material to the sample. The second liquid may cause bonding of the biological material to the surface, or may be a fixative or a stain to fix or stain the biological material. Examples of such fixatives/stains are e.g. formaldehyde, glutaraldehyde, osmium tetroxide, rutheen tetroxide.

In yet another embodiment the surface modification comprises functionalizing the sample by forming active sites caused by the deposition of enzymes, nanowires or other nanostructures, and the second liquid comprises providing a material to said active sites.

These techniques are known to the skilled person preparing biological samples ex-situ under atmospheric conditions. By now applying these techniques in-situ in vacuum, there applicability is enhanced as well as their ease of use.

In still another embodiment the two liquids are provided on one surface, the manipulator movable with respect to said surface.

This surface can be the surface of a sample stage.

In a preferred embodiment the sample surface is during and/or after the modification of the sample surface layer inspected using a beam of charged particles.

In yet another embodiment the liquids are applied using a first liquid injection system and a second liquid injection system.

In a further embodiment the first liquid injection system and the second liquid injection system are integrated in one structural liquid injection system.

This embodiment is particularly useful to avoid positioning two liquid injection systems, as this involves positioning only one system, and thus saves processing time.

It is noted that, to control the evaporation rate, the temperature of the liquids must preferably be well controlled. As an example: the vapour pressure of water at 4° C. is 8.14 hPa and at 20° C. 23.4 hPa. Both the vacuum system of the charged particle apparatus should be capable of handling the amount of evaporated liquid, and the amount of liquid should be large enough so that liquid is present during the whole of the processing time. Although a low temperature (just above the melting point) is favorable for the pressure in the system and the evaporation of the liquid, a high temperature results in a higher reaction rate. Depending on the chemistry used and the effect obtained (modification of the sample surface roughness, the hydrophilicity, surface charge, surface energy, biological compatibility, or reactivity, the addition of functional groups, the addition of biological material, plating the sample surface or the removal of a sample surface layer) an optimum temperature is selected.

Silicon lamellae that are thinned using a focused ion beam suffer from gallium implantation on the surface as well as crystal lattice damage, see for example J. Mayer et al., TEM Sample Preparation and FIB-Induced Damage', MRS BULLETIN, Vol. 32 (May 2007), p. 400-407 [-3-]. A solution is to etch a thin layer of less for example than 10 nm from the lamella. Care should be taken that, if a weld between sample and manipulator is used to connect the two, the processing does not result in a complete removal of the weld, resulting in a disconnect between the sample and the manipulator, and thus a probable loss of the sample. This may be achieved by using a good combination of weld material and liquids, or by only partially dipping the sample in the liquid, keeping the weld free of liquid (keeping in mind the liquid wetting the surface of the sample, if applicable). Also, as the thickness of the weld is typically approximately 1 μm, removal of the weld is unlikely if a much smaller thickness (for example less than 10 nm, or less than 50 nm) is removed from the sample. It is worth mentioning that typically for the removal of the surface layer of a semiconductor sample machined with a focused ion beam a layer of less than 10 nm is removed.

The chemicals used for modification strongly depend on the sample material and the type of modification. As an example some etchants:

TABLE 1

Etchants for different sample materials.

| Sample material | Etchant | Preferred temperature range [° C.] |
|---|---|---|
| Silicon | ~20% KOH in $H_2O$ | +20 to 100 |
| Steel | 4-15% $HClO_4$, 2% butoxyethanol in ethanol | −45 to −40 |
| Tungsten | 0.5-10% NaOH in water | −20 to −10 |
| Aluminium | ~10% $HClO_4$ in ethanol | 0 to 20 |
| Copper | $H_3PO_4$ in ethanol | 0 to 20 |

As the first liquid for these etchants is different (in this example either ethanol or water based), so should the matching second liquid used be chosen accordingly (in this example used for rinsing). The temperature should be chosen to match the demands of modification (for example reaction rate) and allowable evaporation rate. The evaporation rate may be limited by the maximum flow from the liquid injectors/supplies (as at high evaporation rates also a change in concentration of dissolved chemicals may occur, or by the pumping speed of the charged-particle apparatus. Dependent on the use, the first liquid and the second liquid can have the same (controlled) temperature or different (controlled) temperatures.

Likewise plating (chemical or electroplating) chemicals and solvents are known to the skilled person.

Using a first liquid of water or alcohol with dissolved biological material the second material can comprise for example fluorescent proteins, fluorescent markers, electron dense markers (for example silver or gold particles with a diameter of between 5 and 25 nm), attaching themselves to specific sites of the biological material.

It is noted that the definition of fluorescent markers as used here includes organic dyes and inorganic fluorescent markers (quantum dot).

A first liquid comprising enzymes, nanowires or other nanostructures can be used to functionalize the sample (for example form active sites on the sample) to which biological materials in a second liquid can bond.

BRIEF DESCRIPTION OF THE DRAWINGS

The invention is now elucidated using figures, in which identical numerals indicate corresponding figures. To that end.

DETAILED DESCRIPTION OF THE DRAWINGS

Figure 1:
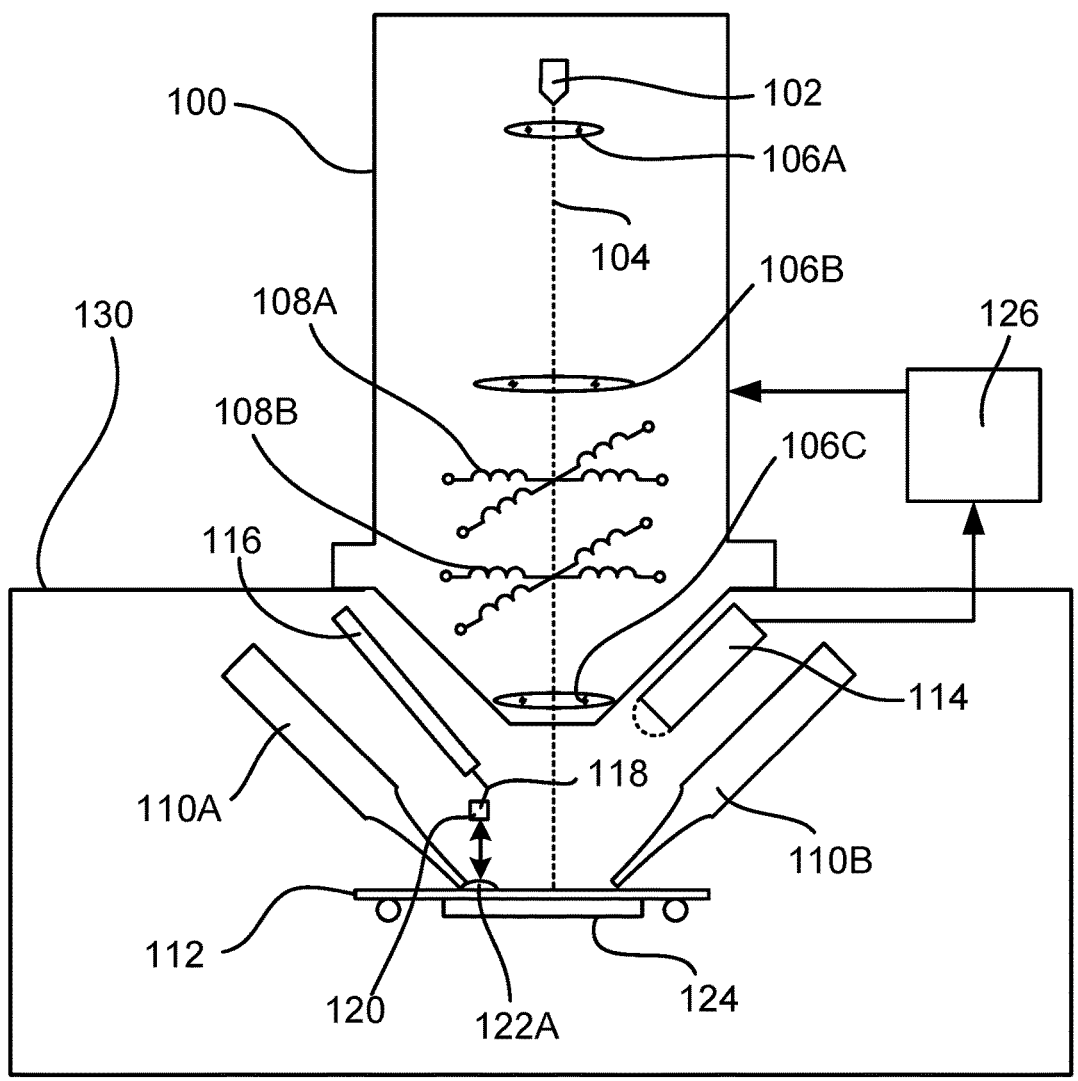
FIG. 1 schematically shows a SEM according to the invention.

FIG. 1 schematically shows a SEM according to the invention.

A SEM column 100 is mounted on a evacuable sample chamber 130. The SEM column comprises an electron emitter 102 producing a beam of energetic electrons 104 with a selectable energy of between 0.2 to 30 keV (note: higher and lower energies are known to be used). This beam of electrons is manipulated by lenses 106A, 106B, 106C and deflected by deflectors 108A, 108B. Lenses and deflectors may be electrostatic or magnetic in nature, and the number of lenses and deflectors may vary. The beam is passed through apertures in diaphragms (not shown), thereby limiting the diameter of the beam as well as limiting the influx of gas into the vacuum of the SEM column.

The beam of electrons exiting the SEM column is directed to the sample stage 112 of the SEM. The stage is typically capable of translation in three directions and tilting round two or three axis. Before inspecting the sample the sample 120, attached to the distal end 118 of a manipulator 116, is dipped in a droplet of a first liquid 122. The droplet of first liquid is obtained out of liquid injector 110A. Likewise a droplet of a second liquid can be obtained out of liquid injector 110B.

After dipping the sample in the first and the second liquid the sample is transported to the position where the beam of electrons intersects the stage. When the beam hits the sample, secondary electrons are emitted, to be detected by, for example, an Everhart-Thornley detector 114, thus enabling inspection of the sample.

To control the evaporation rate of the liquids a Peltier heater/cooler 124 is attached to the stage. Cooling a liquid, ultimately freezing it, lowers the vapour pressure of a liquid, and thus its evaporation rate (in vacuum).

A controller 126 controls the column (including deflectors), acts as signal/image processor for the signal from detector 114, and controls the manipulator, liquid injectors and vacuum pumps (the latter not shown).

It is noted that a liquid injection system is known to the skilled person and commercially available from e.g. Kleindiek Nanotechnik GmbH, Reutlingen, Germany, see http://www.nanotechnik.com/mis-em.html [-4-]. Other injectors may be based on modified gas injection systems (GISses) or on injectors using techniques derived from inkjet printers (for example using piezo-expellers as discussed in U.S. Pat. No. 8,919,902 assigned to Ricoh Company Ltd. [-5-], or thermal bubble expellers as discussed in U.S. Pat. No. 8,919,938 assigned to Hewlett Packard Development Company L.P. [-6-]) or based on electro-spraying from a needle.

It is further noted that, although the above example only mentions an electron beam, likewise apparatuses producing charged particle beam comprising ions are known. The ions can be formed by, for example, a gas discharge source, a liquid metal ion source. The ions can be positive or negative charged ions, and can be multiply charged or single charged ions. Also charged clusters can be generated.

Figure 2:
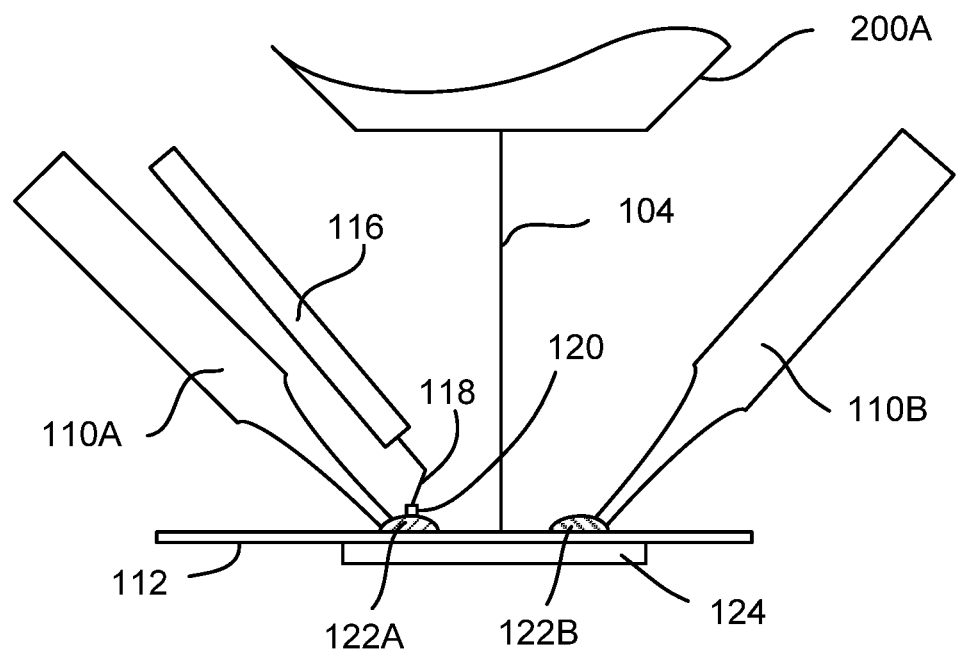
FIG. 2 schematically shows a detail of a SEM according to the invention.

FIG. 2 schematically shows a detail of a SEM according to the invention.

FIG. 2 schematically shows an enlarged view of the area where the liquid droplets are formed. Sample 120 on distal end 118 is seen to be dipped in the liquid droplet 122A. This can be achieved by moving the sample manipulator 116 and the stage 112 with respect to each other, i.e., by moving either the manipulator or the stage. The temperature of the first droplet 122A is regulated by heater 124, and need not be identical to the temperature of the second droplet 122B. The volume of the droplets can be regulated by the supply of the liquid via liquid injection systems 110A and 110B, respectively, the temperature of the droplets, and the composition of the residual gasses in the vacuum surrounding the droplets.

As clear to the skilled artisan the speed of modification of the sample surface is a function of the composition of the liquid (concentration of materials, etc.), the temperature and the period of time the sample is dipped in the liquid. Also movement of the sample within the droplet (thereby influencing the concentration of chemicals near the surface of the sample while the sample is immersed in the droplet) influences the process speed. This can advantageously be used by using e.g. (ultra)sonic excitation of the droplet (e.g. by placing the droplet on a resonating piezo-actuator or, as an alternative, form the extremity of the manipulator to which the sample is attached as a vibrating extremity, or place the whole manipulator on an (ultra)sonic excitator). Also the stage can be equipped to move the liquid.

Figure 3:
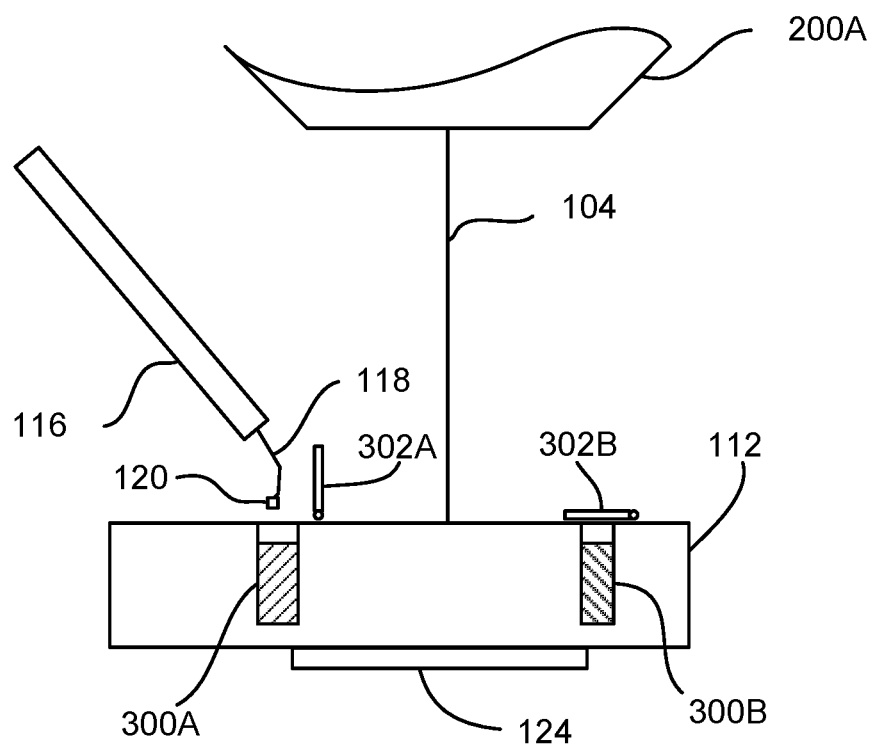
FIG. 3 schematically shows a detail of an alternative arrangement of a SEM according to the invention.

FIG. 3 schematically shows a detail of another embodiment.

FIG. 3 shows an embodiment where no droplets are used, but instead small containers 300A, 300B are used. To avoid continuous evaporation these containers can be closed by lids 302A, 302B, movable by actuators (not shows). The actuators of these lids may employ piezo-actuators, or other means. Also quick temperature control may be used to avoid evaporation when the liquid is not 'in use'.

The size (diameter) of the containers should be sufficiently large that the sample can be dipped in the containers.

It is noted that, in the case that the surface of the liquid is sufficiently removed from the surface of the sample stage 112, a higher temperature of the liquids can be combined with a low temperature of the channels, leading to a reduced evaporation rate, as the vapour condenses on the walls of the channels.

The skilled artisan will recognize that more than two liquids can be used, and that also before, in-between or after dipping the sample in the liquids the sample may be inspected, exposed to gas, exposed to for example BID (beam induced deposition, using either an ion beam, electron beam or a laser beam), exposed to a plasma, etc.

The method enables the wet processing of a sample in-situ, thereby enhancing speed (as the sample need not be taken out of the vacuum chamber) and/or avoiding subsequent alteration/contamination of the sample, such as oxidation, etc.

The method is particularly useful for etching a lamella after machining the lamella with a (gallium) FIB to remove the surface layer where gallium implantation took place, or where the crystal lattice is disturbed.

CITED LITERATURE

[-1-] S J Randolph et al., 'Capsule-free fluid delivery and beam-induced electrodeposition in a scanning electron microscope', RSC Adv., 2013, p 20016-23.
[-2-] U.S. Pat. No. 5,270,552 assigned to Hitachi.
[-3-] J. Mayer et al., TEM Sample Preparation and FIB-Induced Damage', MRS BULLETIN, Vol. 32 (May 2007), p. 400-407.
[-4-] http://www.nanotechnik.com/mis-em.html
[-5-] U.S. Pat. No. 8,919,902 assigned to Ricoh Company Ltd.
[-6-] U.S. Pat. No. 8,919,938 assigned to Hewlett Packard Development Company L.P.

The invention claimed is:

1. Method of modifying a sample surface layer from a sample in a particle-optical apparatus, the method performed in vacuum, the method comprising:
   providing the sample attached to a manipulator,
   providing a first liquid at a first temperature, the first liquid including an etchant;
   dipping the sample in the first liquid in a vacuum chamber of the particle-optical apparatus, thereby causing the sample surface layer to be etched,
   removing the sample from the first liquid using the manipulator,
   providing a second liquid, different from the first liquid, at a second temperature, the second liquid including a rinsing solution comprising ethanol or water, the second liquid being matched to the first liquid;
   dipping the sample in the second liquid in the vacuum chamber to rinse the sample, and
   removing the sample from the second liquid
   in which the sample is a semiconductor lamella having gallium implantation and causing the sample surface layer to be etched includes etching less than 50 nm from the lamella surface to remove the implanted gallium.

2. The method of claim 1 in which the sample is attached to the manipulator by forming a weld using beam induced deposition, the beam induced deposition induced by a laser beam, an electron beam or an ion beam.

3. The method of claim 1 in which the sample has a dimension of less than 10 μm in any direction and the first liquid and the second liquid are deposited as droplets with a volume of less than 1 picoliter.

4. The method of claim 1 in which the step of providing the sample attached to a manipulator comprises the steps of:
   providing a work piece,
   attaching the sample to the manipulator, and
   excising the sample from the work piece using a focused ion beam in the vacuum chamber.

5. The method of claim 1 in which dipping the sample in the first liquid in a vacuum chamber of the particle-optical apparatus thereby causing the sample surface layer to be etched includes electro-chemical etching, said electro-chemical etching using a non-virtual cathode.

6. The method of claim 5 in which the thickness of the removed sample surface layer is less than 10 nm.

7. The method of claim 1 in which the sample is rinsed repeatedly.

8. The method of claim 1 in which the two liquids are provided on one surface, the manipulator movable with respect to said surface.

9. The method of any claim 1 in which the liquids are applied using a first liquid insertion system and a second liquid insertion system.

10. The method of claim 1 in which the second temperature is different from the first temperature.

11. The method of claim 10 in which the rate of evaporation of the first liquid and the second liquid is controlled by controlling the temperatures of the first liquid and the second liquid.

12. The method of claim 1 in which dipping the sample in the first liquid in a vacuum chamber of the particle-optical apparatus, thereby causing the sample surface layer to be etched comprises controlling the amount of etching by controlling the submerging time, the first liquid concentration, or the first liquid temperature.

13. The method of claim 1 in which the etchant comprises KOH, HClO4, butoxyethanol, NaOH, or H3PO4.

* * * * *